(12) United States Patent
Lange et al.

(10) Patent No.: US 7,341,600 B2
(45) Date of Patent: Mar. 11, 2008

(54) CYLINDRICAL FIBER REINFORCED IMPLANT

(75) Inventors: Robert Lange, Paris (FR); Steve Olson, Corona, CA (US)

(73) Assignee: Co-Ligne AG, Zürich (CH)

( * ) Notice: Subject to any disclaimer, the term of this patent is extended or adjusted under 35 U.S.C. 154(b) by 405 days.

(21) Appl. No.: 10/737,723

(22) Filed: Dec. 17, 2003

(65) Prior Publication Data

US 2004/0210311 A1    Oct. 21, 2004

(30) Foreign Application Priority Data

Dec. 17, 2002    (EP)    ................... 02406104

(51) Int. Cl.
*A61F 2/44* (2006.01)
(52) U.S. Cl. .................. 623/17.11
(58) Field of Classification Search ............. 623/17.11, 623/16.11, 17.12, 17.15, 17.16, 23.5, 23.51, 623/23.52, 23.54
See application file for complete search history.

(56) References Cited

U.S. PATENT DOCUMENTS 4,911,718 A * 3/1990 Lee et al. ................. 623/17.15

| 5,192,327 | A | 3/1993 | Brantigan |
| 5,211,664 | A * | 5/1993 | Tepic et al. ............... 623/16.11 |
| 5,429,863 | A | 7/1995 | McMillin |
| 5,906,616 | A | 5/1999 | Pavlov et al. |
| 5,968,098 | A | 10/1999 | Winslow |
| 6,224,631 | B1 * | 5/2001 | Kohrs ..................... 623/17.11 |

FOREIGN PATENT DOCUMENTS

| EP | 0551611 | 7/1993 |
| EP | 1236451 | 9/2002 |
| WO | WO-9846169 | 10/1998 |

* cited by examiner

*Primary Examiner*—Eduardo C. Robert
*Assistant Examiner*—David Comstock
(74) *Attorney, Agent, or Firm*—Browdy and Neimark, PLLC

(57) ABSTRACT

The cylindrical fiber reinforced implant is designed to be inserted between two adjacent vertebrae. The implant having an outer wall with a general cylindrical or oval shape and preferably an open volume for bone filling. Said wall having reinforcing fibers which at least in part are oriented in a first direction. A support extending within said volume having reinforcing fibers which are at least in part oriented in a second direction, said first and said second directions are different. Preferably the fibers of the outer wall are at least partly concentrically oriented. The support is preferably a separately formed part, that is inserted into the outer wall.

17 Claims, 2 Drawing Sheets

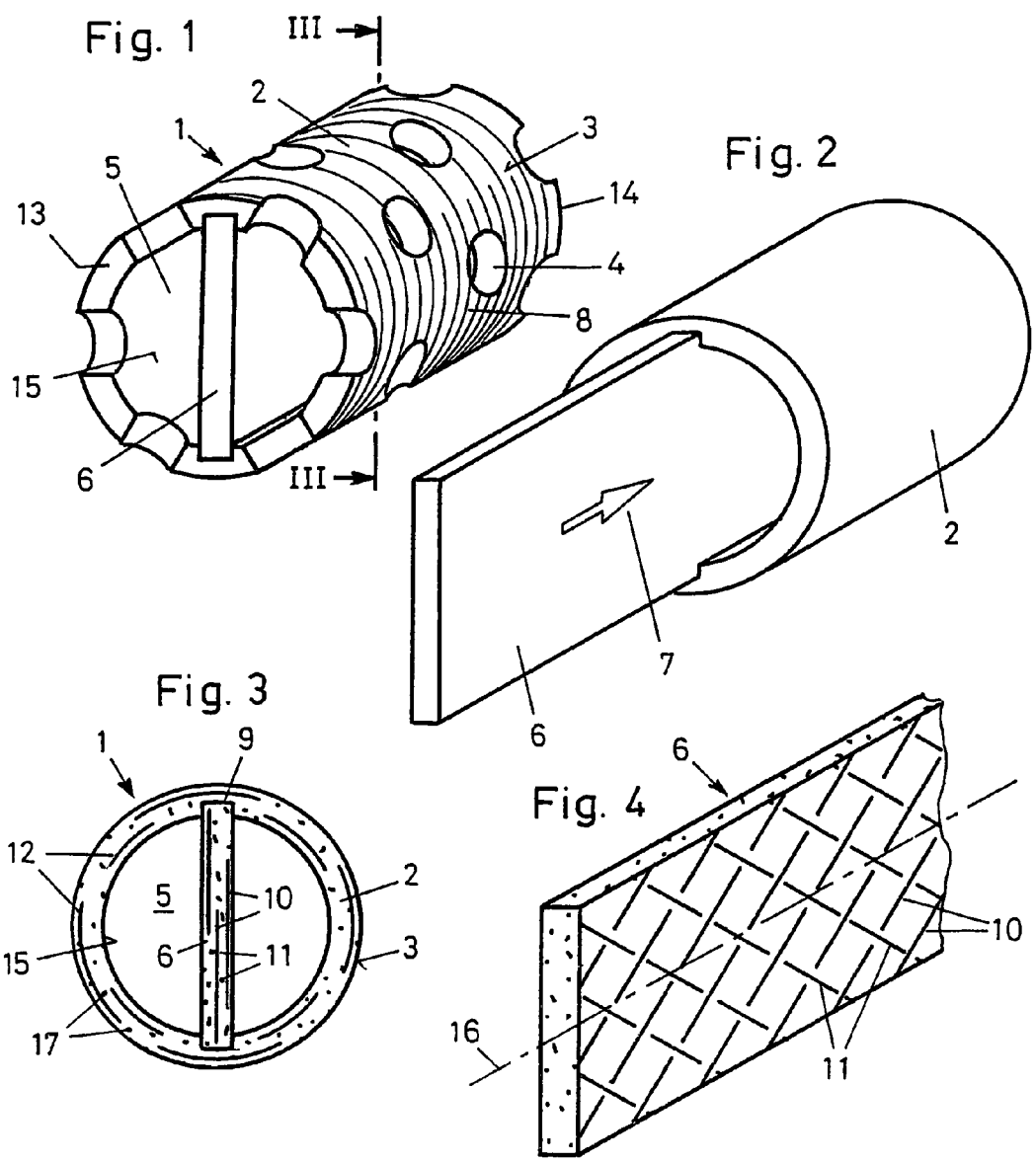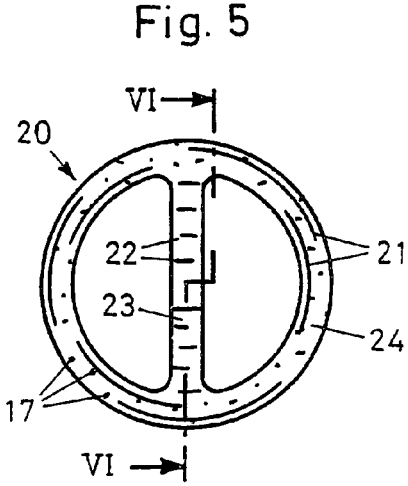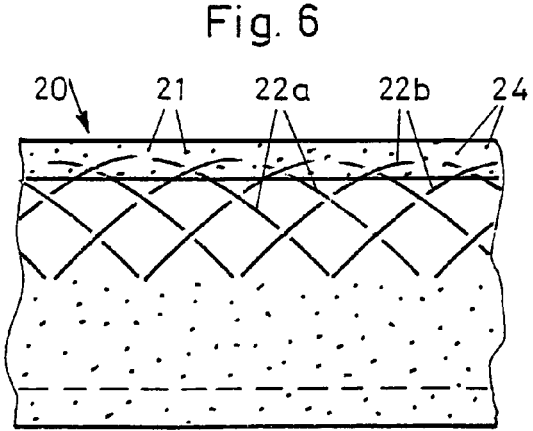

CYLINDRICAL FIBER REINFORCED IMPLANT

BACKGROUND OF THE INVENTION

1. Technical Field of the Invention

The present invention relates to a three-dimensional fiber reinforced implant, particularly a vertebral cage for insertion between two adjacent vertebra.

2. Prior Art

Fiber reinforced implants are well known. U.S. Pat. No. 5,429,863 for example discloses a vertebral implant cage, that is fabricated from a block, which is a fiber reinforced composite structure. Carbon fibers are located in every part of the block and randomly interlocked. The cage may have the shape of a cylindrical rod and is provided with cavities which are filled with bone material and is designed to be inserted between adjacent vertebrae.

U.S. Pat. No. 5,906,616 discloses a conically-shaped fusion cage provided with a thread formed as a part of an external conical surface. Apertures provide for bone growth between the engaged vertical bone and bone material packed within the cage.

U.S. Pat. No. 5,968,098 discloses a fusion cage having a generally elliptical cross-section. It includes an entry end portion, a trailing end portion and a thread as a part of an external conical surface. The cage is preloaded with bone material and inserted into the desired surgical location with well known surgical instruments.

A fusion cage formed of radiolucent material is also disclosed in EP-A-0 307 241. The cage has a roughened outer surface for receiving bone in-growth and end faces with means securing it on a tool for insertion on the desired site of the vertebrae.

The role of a vertebral implant is to stabilize a vertebral segment and to bear load while the surrounding bone consolidates, taking over the mechanical function with a viable bone fusion. On one hand the implant must be robust enough to bear rotation at insertion, and axial load, sheer and fatigue during weight bearing. On the other, the implant must provide enough space for bone graft to grow through or around the device. Thus cage designers are faced with a trade off what makes the implant bear load, and the bone ports which must carry enough bone tissue required for bone consolidation. Furthermore, it has been postulated that stress shielding in an implant may prevent fusion of viable bone through the implant, and strength and stiffness should be as close to the surrounding bone tissue as possible.

Several materials are used for inter-body cages and most commonly are Titanium Alloy, PEEK as well as carbon composite. Titanium, while certainly strong enough for the application, has the disadvantage of being a radiographically opaque, making it impossible to visualize if bone has grown through the cage with standard x-ray. It is also known that titanium also produces artificiats for other radiographic examinations such as C.T. or MRI.

OBJECT AND SUMMARY OF THE INVENTION

It is an objective of the present invention to provide a three-dimensional fiber reinforced implant, that is radiolucent and provides increased mechanical performance, while at the same time maximizes the space for bone graft.

Cylindrical implants have the advantage of easier insertion. Both the reaming and interspace preparation and cage insertion are performed with a twisting motion.

Square or rectangular cages, on the other hand, can be more easily reinforced with vertical struts. To prevent collapse of cylindrical cages, wall thickness is increased that reduces cavity size preventing the formation of viable bone. The invention described herein, through the use of selectively orienting the fibers in the various cage components has contributed a cage resistant to collapse and rotation, but preserves an ample cavity for bone.

The implant according to the present invention is provided with a support extending within the outer wall and has reinforcing fibers which are at least in part oriented in a direction which is different to the orientation of fibers embedded into the outer wall. The additional orientation of the fibers within the support prevents a deformation of the implant to where the fibers of the outer wall are bent beyond the point of failure. Deformation beyond the point of breakage is prevented in axial load, bending, rotation, impact and shear.

The support is preferably a separately formed part, that is inserted into the outer wall, but can be also a part of the outer wall.

BRIEF DESCRIPTION OF THE DRAWINGS

Other advantages and features of the present invention will be apparent to those skilled in the art after reading the following specification with reference to the accompanying drawings.

FIG. 1 is a schematic perspective view of a fiber reinforced cage of this invention, FIG. 2 is a schematic perspective view of the cage according to FIG. 1 wherein the support is partly withdrawn from the outer wall, FIG. 3 is a section along line III-III of FIG. 1, FIG. 4 is a schematic perspective view of a part of the support as seen in FIG. 3, FIG. 5 is a plan view of a further embodiment of the invention, FIG. 6 is a cross-section along line VI-VI of FIG. 5.

DETAILED DESCRIPTION OF THE PREFERRED EMBODIMENT(S) OF THE INVENTION

Figure 7:
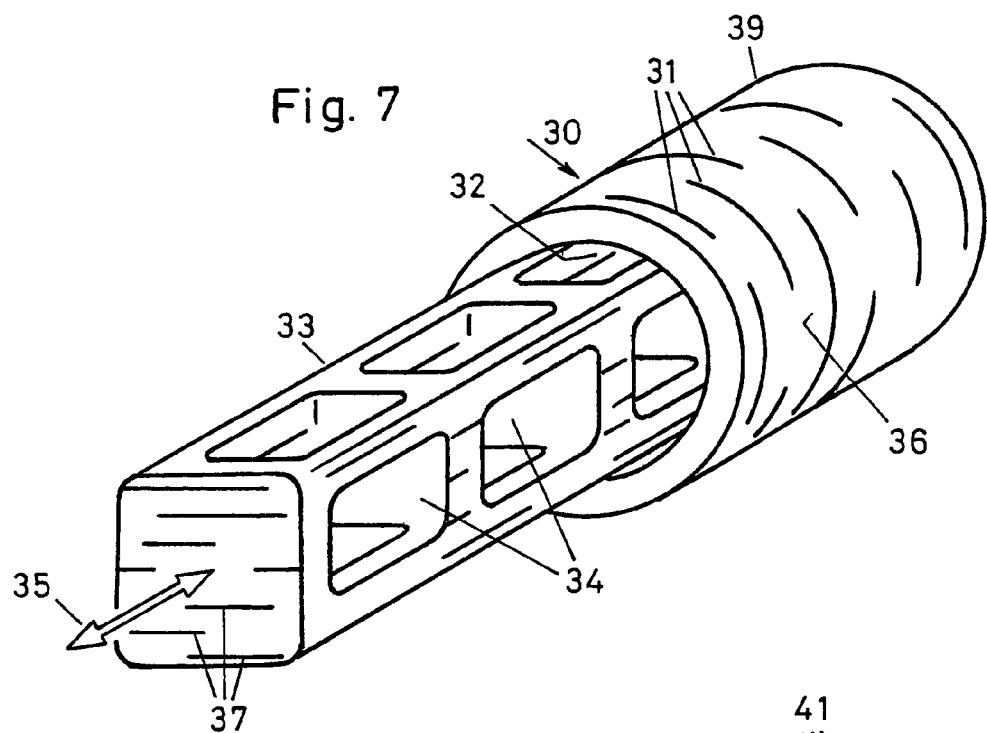
FIG. 7 is a schematic perspective view of a cage according to a further embodiment of the invention.

Referring now to the drawings wherein like numerals indicate like parts, the cage of this invention is depicted by the numeral 1. The cage 1 has a pair of front surfaces 13 and 14, an outer surface 3 and an inner surface 15. A cylindrical outer wall 2 has several perforations or ports 4 which connect the outer surface with the cavity and which enable fusion of bone through the cage. Further, the outer surface 3 is provided with a thread 8. The cage is packed with bone chips or bone substitute not shown in the drawing.

A support 6 having the shape of a plate is inserted into grooves 9 of the cavity 5. The support 6 is inserted in the longitudinal direction of the outer wall 2, as indicated with arrow 7. The outer wall 2 as well as the support are made from carbon fiber composite. Fibers 10 and 1 are preferably oblique to the longitudinal direction but may also be perpendicular to the longitudinal direction. In FIG. 4 the longitudinal direction is indicated with line 16. Fibers 10 and 1 within the support have preferably two directions of orientation as shown in FIG. 4 and can run along the entire length of the support 6. The matrix of the support 6 as well as the outer wall 2 are made from PEEK or PEKEKK preferably from commercially available Osta-PEK®.

Long fibers in the support 6 can extent completely along the axis of the part that provides optimal strength and regularity of the mechanical properties of the implant. The same is there on the concentric fibers. These can wind up around the cylinder several times within the part and opposing fibers can cross the entire part in a different direction. Cross direction holds the part together and allowing it to resist loads that will be subject to the implant from different directions. The difference in mechanical properties between short carbon fiber composite and long fiber composite in a controlled orientation can be compared to particle board and the structure in well carpentered oak. Particle board is held together by glue, while the oak structure uses fabric orientation of wood to oppose the forces and subjected upon the structure.

Fibers 12 and 17 within the outer wall 2 are preferably concentrically and/or longitudinally oriented. The fibers 12 are preferably long fibers and may run along the entire circumference of the outer wall. The fibers 17 are as well preferably long fibers and may run in the longitudinal direction along the entire length. It is an important aspect of the invention, that the fibers 10 and 11 of the support 6 and the fibers 12 of the outer wall 2 have different orientations. The additional orientation of the fibers 10 and 11 prevents deformation of the cage 1 to where the fibers 12 are bent beyond the point of failure. The fibers 12 need not always be concentrically oriented and could be also parallel to the longitudinal direction 16. Furthermore, part of the fibers could be concentrically oriented and another part of the fibers could be parallel to the longitudinal direction 16.

FIGS. 5 and 6 disclose a cage 20 having a wall 24 with a generally round cross-section and a support 23 integrally connected to the wall 24. The cage 20 is formed of radiolucent material and contains imbedded long reinforcing fibers 21 and 22. The fibers 21 of the wall 24 are generally concentrically oriented or parallel to the longitudinal direction 16. The fibers 22 of the support 6 have at least one additional orientation, that is preferably oblique to the longitudinal direction 16. As shown in FIG. 6, Fibers 22a may have an orientation different to that of fibers 22b. Fibers 22 could be also perpendicular to the longitudinal direction 16.

FIG. 7 shows a cage 30, that is also formed of radiolucent material and contains fibers 31 and 37 with different orientations. The cage is made of two parts, an outer wall 39 having a generally round or oval cross-section and a box-like support 33, that slides in the wall 39 like a drawer. Apertures 34 within the support 33 provide for bone growth and can be preloaded with bone material. The wall 39 can also have not shown apertures for bone growth and a thread as a part of an external surface 36. The fibers 31 are preferably oriented in concentric circles whereas the fibers 37 have an additional orientation, for example perpendicular to the longitudinal direction 16.

Figure 8:
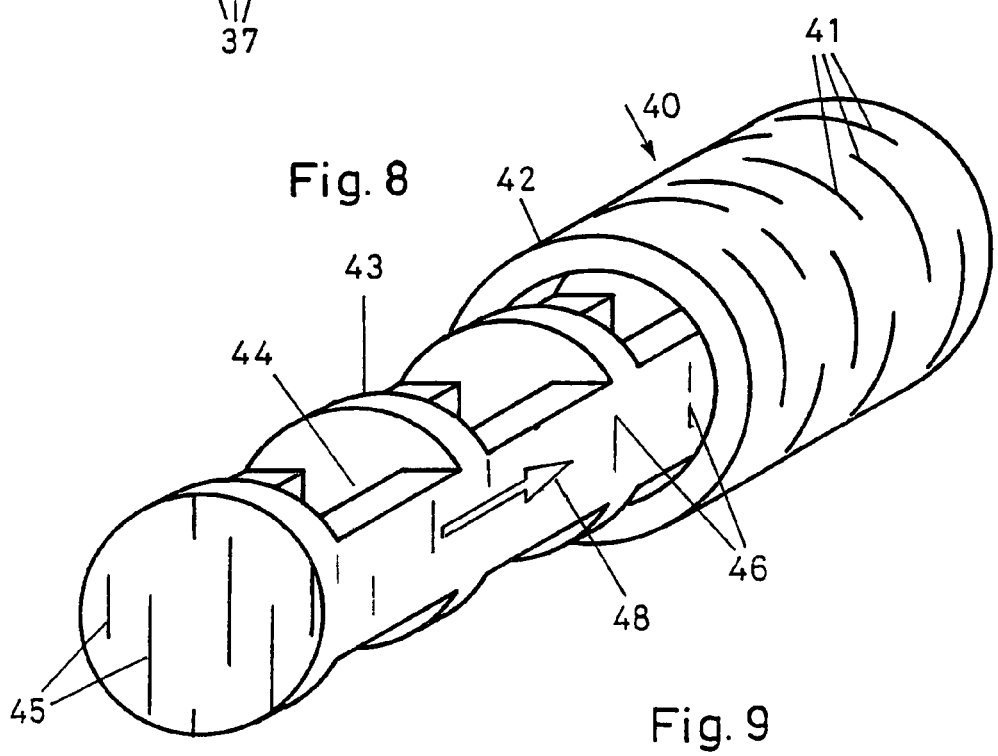
FIG. 8 is a schematic perspective view of a cage according to a further embodiment of the invention and FIG. 9 illustrates the orientation of the fibers in the cage according to FIG. 8.
Figure 9:
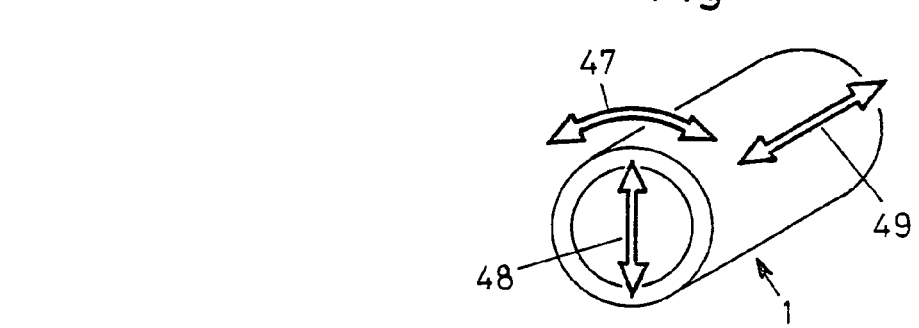

FIG. 8 shows a cage 40, that is also made of two parts, an outer wall 42 and a support 43, that is an insert and contains fibers 45 and 46 which are vertically oriented, but which may have different orientations. The outer wall 42 contains concentrically oriented fibers 41 and has a generally round or oval cross-section. The support 43 is provided with apertures 44 which can be preloaded with bone material and slides in the outer wall 42 like a drawer, as indicated with arrow 48. The fibers 45 and 46 are preferably long carbon fibers and have different orientations to each other and to the fibers 41. The fibers 45 and 46 are vertically oriented, and the fibers 46 are parallel to the longitudinal direction 16. In FIG. 9 the orientations of the fibers 41, 45 and 46 are schematically indicated with arrows 47 to 49.

The invention claimed is:

1. Three-dimensional fiber reinforced implant, optionally a vertebral cage adapted to be inserted between two adjacent vertebrae,
   the implant having an outer wall with a general cylindrical shape and optionally an open volume for bone filling,
   said outer wall having a matrix with embedded reinforcing fibers which at least in part are oriented in a first direction,
   a support capable of preventing deformation of the implant, the support extending within said volume having a matrix with embedded reinforcing fibers which are at least in part oriented in a second direction,
   said first and said second directions being different,
   wherein the support comprises a planar strut which extend coaxially through the axis of the outer wall and diametrically between opposite inner sides of said outer wall; and
   wherein the fibers of the outer wall are at least partly concentrically oriented.

2. Implant according to claim 1, wherein the fibers of the outer wall are at least partly parallel oriented.

3. Implant according to claim 2 wherein the fibers of the support are at least partly parallel oriented.

4. Implant according to claim 1, wherein the fibers of the support are at least partly parallel oriented.

5. Implant according to claim 1, wherein the support is a separate insert.

6. Implant according to claim 5 wherein the support is slidable within said volume, optionally having a circular cross-section.

7. Implant according to any of the claim 1, wherein the support is slidable within longitudinal grooves in the inner sides of the outer wall.

8. Implant according to claim 7, wherein the support in part has a circular cross-section.

9. Implant according to claim 1, wherein the fibers of said outer wall are at least partly concentrically and the fibers of the support are at least partly longitudinally oriented.

10. Three-dimensional fiber reinforced implant, optionally a vertebral cage adapted to be inserted between two adjacent vertebrae,
the implant having an outer wall with a generally cylindrical or oval shape and an open volume for bone filling, said wall having reinforcing fibers which are mainly concentrically oriented,
a support extending within said volume, wherein
the support contains reinforcing fibers which are mainly oriented in a direction different from the direction of the fibers of the outer wall,
wherein the support is a planar strut which extends coaxially through the axis of the outer wall and between opposite inner sides of the outer wall.

11. Implant according to claim 10, wherein the fibers of the outer wall are parallel oriented.

12. Implant according to claim 10, wherein the fibers of the support are parallel oriented.

13. Implant according to claim 10, wherein the support is a separate insert.

14. Implant according to claims 11 or 13, wherein the fibers of the support are parallel oriented.

15. Implant according to claim 10, wherein the support is slidably inserted within said volume.

16. Implant according to claim 15, wherein the support in part has a circular cross section.

17. Implant according to claim 10, wherein the direction of the fibers of the support is oblique or perpendicular to the longitudinal direction of the support.

* * * * *